(12) United States Patent
Webb et al.

(10) Patent No.: US 8,553,337 B2
(45) Date of Patent: Oct. 8, 2013

(54) MULTI-PATH, MULTI-MAGNIFICATION, NON-CONFOCAL FLUORESCENCE EMISSION ENDOSCOPY APPARATUS AND METHODS

(75) Inventors: Watt W. Webb, Ithaca, NY (US); Chris Xu, Ithaca, NY (US)

(73) Assignee: Cornell University, Ithaca, NY (US)

(*) Notice: Subject to any disclaimer, the term of this patent is extended or adjusted under 35 U.S.C. 154(b) by 13 days.

(21) Appl. No.: 12/742,562

(22) PCT Filed: Nov. 12, 2008

(86) PCT No.: PCT/US2008/083164
§ 371 (c)(1),
(2), (4) Date: May 12, 2010

(87) PCT Pub. No.: WO2009/064746
PCT Pub. Date: May 22, 2009

(65) Prior Publication Data
US 2010/0261958 A1    Oct. 14, 2010

Related U.S. Application Data

(60) Provisional application No. 60/987,270, filed on Nov. 12, 2007, provisional application No. 60/987,868, filed on Nov. 14, 2007.

(51) Int. Cl.
*G02B 3/00* (2006.01)
*G02B 17/00* (2006.01)

(52) U.S. Cl.
USPC ............ 359/722; 359/730; 359/731; 359/736

(58) Field of Classification Search
USPC ................. 359/722, 726, 727, 730, 731, 733, 359/736, 793, 796
See application file for complete search history.

(56) References Cited

U.S. PATENT DOCUMENTS

| 3,170,025 A | 2/1965 | Ino |
| 3,931,536 A | 1/1976 | Fohl et al. |

(Continued)

FOREIGN PATENT DOCUMENTS

WO     WO 9918845     4/1999

OTHER PUBLICATIONS

Flushberg et al.; Fiber-optic fluorescence imaging; Nature Methods; vol. 2, No. 12; Nature Publishing Group; Nov. 18, 2005; 941-950.

(Continued)

*Primary Examiner* — Jack Dihn
(74) *Attorney, Agent, or Firm* — William Greener; Bond, Schoeneck & King PLLC (57) ABSTRACT

Embodiments of the invention include an optical system and an optical system module, coupled to a distal end of a fluorescence emission endoscope apparatus, an optical waveguide-based fluorescence emission endoscopy system, and a method for remotely-controlled, multi-magnification imaging of a target or fluorescence emission collection from a target with a fluorescence emission endoscope apparatus. An exemplary system includes an objective lens disposed in a distal end of an endoscope apparatus. The lens is adapted to transmit both a visible target illumination and a fluorescence-emission-inducing target illumination as well as fluorescence-emission and visible light from the target. The system can thus simultaneously provide low magnification, large field of view imaging and high magnification, high-resolution multiphoton imaging with a single lens system.

8 Claims, 6 Drawing Sheets

(56) References Cited

U.S. PATENT DOCUMENTS

| | | | |
|---|---|---|---|
| 4,976,522 A | 12/1990 | Igarashi | |
| 5,179,468 A | 1/1993 | Gasloli | |
| 5,191,203 A | 3/1993 | McKinley | |
| 5,323,009 A | 6/1994 | Harris | |
| 5,703,724 A | 12/1997 | Miyano | |
| 5,705,882 A | 1/1998 | Oughton | |
| 5,743,846 A | 4/1998 | Takahashi | |
| 5,808,808 A | 9/1998 | Yamanashi | |
| 5,828,498 A | 10/1998 | Sekiya et al. | |
| 5,907,425 A | 5/1999 | Dickensheets et al. | |
| 5,921,926 A | 7/1999 | Rolland | |
| 5,995,279 A | 11/1999 | Ogino et al. | |
| 6,104,945 A | 8/2000 | Modell | |
| 6,124,597 A | 9/2000 | Shehada | |
| 6,134,056 A | 10/2000 | Nakamuka | |
| 6,146,593 A | 11/2000 | Pinkel | |
| 6,411,835 B1 | 6/2002 | Modell | |
| 6,571,118 B1 | 5/2003 | Utzinger | |
| 6,600,943 B1 | 7/2003 | Kiuchi et al. | |
| 6,694,176 B1 | 2/2004 | Tsujita et al. | |
| 6,721,101 B2 * | 4/2004 | Daniell | 359/626 |
| 6,819,361 B1 | 11/2004 | Lee et al. | |
| 6,844,976 B1 | 1/2005 | Firon et al. | |
| 6,949,069 B2 | 9/2005 | Farkas et al. | |
| 6,975,898 B2 | 12/2005 | Seibel | |
| 7,006,141 B1 | 2/2006 | Neil et al. | |
| 7,038,722 B2 | 5/2006 | Kitagishi et al. | |
| 7,091,500 B2 | 8/2006 | Schnitzer | |
| 7,218,454 B2 | 5/2007 | Miyano | |
| 7,256,949 B2 | 8/2007 | Ohshita et al. | |
| 7,411,729 B2 | 8/2008 | Lyama et al. | |
| 7,430,009 B2 | 9/2008 | Kokuwa et al. | |
| 7,502,182 B2 | 3/2009 | Miyano | |
| 7,508,599 B2 | 3/2009 | Ohshita et al. | |
| 7,605,990 B2 | 10/2009 | Liang et al. | |
| 7,626,764 B2 | 12/2009 | Lin et al. | |
| 2003/0174409 A1 | 9/2003 | Nagaoka | |
| 2004/0156124 A1 | 8/2004 | Okada | |
| 2007/0058072 A1 | 3/2007 | Lee | |
| 2008/0100910 A1 | 5/2008 | Kim et al. | |
| 2009/0201360 A1 | 8/2009 | McClatchie | |
| 2009/0203963 A1 | 8/2009 | Ito | |

OTHER PUBLICATIONS

Deisseroth et al.; Next-Generation Optical Technologies for Illuminating Genetically Targeted Brain Circuits; The Journal of Neuroscience; Oct. 11, 2006; 26(41):10380-10386.

Jung et al.; In Vivo Mammalian Brain Imaging Using One- and Two-Photon Fluorescence Microendoscopy; Journal of Neurophysiology; 92: 3121-3133; 2004.

Zipfel et al.; Nonlinear magic: multiphoton microscopy in the biosciences; Nature Biotechnology; vol. 21; No. 11; Nov. 2003.

Zipfel et al.; Live tissue instrinsic emission microscopy using multiphoton-excited native fluorescence and second harmonic generation; PNAS; Jun. 10, 2003; vol. 100; No. 12.

Zipfel et al.; Supporting information for Zipfel et al. (2003) Proc. Natl. Acad. Sci. USA; PNAS Online.

El Ferradi, Nabil; Objective Lens for a Miniature Endoscopic Confocal Microscope; Montana State University; Bozeman, Montana; Jan. 2005; 1-64.

Murakami et al.; A Miniature Confocal Optical Microscope with MEMS Gimbal Scanner; IEEE; 2003' 587-590.

* cited by examiner

MULTI-PATH, MULTI-MAGNIFICATION, NON-CONFOCAL FLUORESCENCE EMISSION ENDOSCOPY APPARATUS AND METHODS

CROSS-REFERENCE TO RELATED APPLICATIONS

This application claims priority to U.S. Provisional application Ser. No. 60/987,868 filed on Nov. 14, 2007, and to U.S. Provisional application Ser. No. 60/987,270 filed on Nov. 12, 2007, the subject matters of which are incorporated by reference herein in their entireties.

STATEMENT REGARDING FEDERALLY SPONSORED RESEARCH OR DEVELOPMENT

This invention was made with government support under Grant No. 1R01EB006736-01 and Grant No. 5-P41EB001976 sponsored by the National Institute of Biological Imaging and Bioengineering at the National Institutes of Health. The government has certain rights in the invention.

BACKGROUND OF THE INVENTION

1) Field of the Invention

Embodiments of the invention are most generally related to the field of multiphoton fluorescence and/or non-linear harmonic emission endoscopy apparatus and methods. More particularly, embodiments of the invention are directed to multi-magnification, non-confocal, multi-path optical systems and optical system modules for use with fluorescence emission endoscopy systems, and associated methods.

2) Description of the Related Art

The multiphoton microscope was co-invented almost two decades ago by Dr. Watt Webb, a co-inventor of the present invention. Multiphoton microscopy (MPM), as is now well known, is a special kind of laser scanning microscopy that provided significant advantages over standard confocal microscopy. In confocal microscopy, one photon of high energy light (at, e.g., 488 nm) is used to excite a molecule to produce one photon of fluorescence. The light excites molecules in a relatively large region around the focal point. The use of high energy light could easily damage living tissue in the entire region of exposure. Furthermore, imaging depth was limited to about 50 microns ($\mu$) (about five cell layers).

In MPM, multiple low energy photons (at, e.g., 960 nm) impinge on a fluorescent molecule simultaneously, producing one photon of fluorescence from the focal volume of the excitation field. Advantageously, MPM is safer and more efficacious than confocal microscopy for human use because of, e.g., limited site photo-toxicity and photo-damage to living tissue, imaging depths up to 500 to 1000 $\mu$, and lower out-of-focus fluorescence background. Intrinsic fluorescence of certain tissue structures generated by the excitation field reduces or eliminates the need for dye (fluorophore) injection. There are other reasons known in the art. As a result, MPM provides the capability to acquire high contrast, high resolution images, without the need to use pinhole apertures or other spatial filtering elements, with reduced tissue photo-bleaching and photo-destruction that occur from repeated excitation.

The laser light used to generate multiphoton excitation also supports the non-linear optical phenomenon known as harmonic generation. Second harmonic generation (SHG) (and higher-order harmonic generation) under multiphoton excitation can cause collagen and certain tissue structures such as microtubule bundles, nerves and cartilage, for example, to emit intrinsic SHG radiation.

The present inventors, and others, have recognized that various advantages and benefits could be realized by incorporating the principles of MPM into an endoscope. For example, disease diagnosis has for a long time been, and continues to be, carried out by various biopsy procedures. A biopsy requires the physical removal of a (deep) tissue sample from a patient, sample analysis by a pathologist, and reporting, which may take from a few hours to several days or more. The ability to perform real time, in-situ endoscopy in combination with the diagnostic capabilities of multiphoton (and/or harmonic generated) fluorescence imaging could significantly reduce the pain, time, and cost associated with conventional biopsy procedures and assist in disease diagnosis and the extent of tissue damage due to disease states. High resolution MPM endoscopy for sub-tissue, nerve, and cartilage examination offers advantages over the capabilities of current surgical endoscopes. The ability to see nerves and collagen clearly would be especially valuable, for example, in nerve-sparring prostate surgery, bladder cancer treatment, and in maxillofacial and oral surgery.

The simultaneous demands of low magnification, large field of view imaging and high magnification, high-resolution multiphoton imaging necessitate two effective optical imaging systems (e.g., two objective lenses). Although multi-optical systems are routinely provided in microscopy apparatus, separate, switchable optical systems do not provide a suitable architecture for a compact endoscope.

Efforts to date to improve endoscopic imaging procedures and apparatus have focused on the multiphoton fluorescence excitation processes with little attention directed to improved systems and methods for acquiring, identifying, and analyzing the fluorescence, or to improved systems and methods to reduce the severity and invasiveness of existing procedures.

In view of the aforementioned challenges and shortcomings associated with fluorescence emission endoscopy imaging apparatus and methods, the inventors have recognized the unfilled need for apparatus and methods that can address these challenges and shortcomings, and others, in a practical, cost effective, and efficacious manner.

The inventors have also recognized that conventional confocal-based endoscopy imaging apparatus and methods can be disadvantageous due, for example, to image obstruction from scanner apparatus and inefficient signal collection and/or transmission via a concentric excitation fiber waveguide.

Embodiments of the invention are directed to apparatus and methods that address the foregoing mentioned shortcomings and disadvantages associated with current technology in this field.

SUMMARY OF CERTAIN DESCRIPTIVE, ILLUSTRATIVE, AND EXEMPLARY EMBODIMENTS OF THE INVENTION

As used herein, the term "fluorescence emission" will be used to refer to multiphoton (particularly, two-photon but not excluding higher order) fluorescence emission as well as optical second harmonic generation (SHG) (but not excluding higher-order harmonic generation) from a target medium under conditions suitable to excite such fluorescence emission.

Illustrative embodiments of the invention include, but are not limited to, an optical system disposed in, or at, a distal end of a fluorescence emission endoscope, an optical system module for use in, or with, a fluorescence emission endoscope, an optical waveguide-based fluorescence emission endoscopy system, and a method for remotely-controlled, multi-magnification imaging of a target or fluorescence emission collection from a target with a fluorescence emission endoscope apparatus.

An embodiment of the invention is an optical system disposed in, or at, a distal end of a fluorescence emission endoscope apparatus. The optical system includes an objective lens component disposed adjacent a distal end of the endoscope, wherein the objective lens component has a proximal surface that is only partially coated with a patterned coating that at least selectively reflects or transmits a target illumination or selectively transmits or reflects a target emission, and a distal surface that is only partially coated with the coating. According to an aspect, the target illumination is laser-emitted, IR bandwidth, fluorescence-excitation light. In an aspect, the target illumination is visible light, in combination with the IR fluorescence-excitation light. Accordingly, the target emission can be from visible light and/or from fluorescence emission. According to an aspect, the optical system incorporates a light pipe that transmits the target illumination and the target emission. In an aspect, the patterned coating on the proximal surface of the lens component is an annular, circumferential pattern. In a related aspect, the partially coated distal surface of the lens component has only a defined central region that is coated. According to an aspect, a central region of the distal surface of the lens component has a shape that provides a cavity in the distal surface of the lens. In another aspect, a distal lens is fixedly disposed in the cavity in the distal surface of the lens component. In a related aspect, at least a portion of a surface of the distal lens has a coating that at least transmits or reflects at least the illumination light or the emission light. According to various aspects, the proximal surface of the lens component has a spherical or an aspheric shape, and the distal surface of the lens component has a partially flat surface, at least a partially spherical surface shape, or at least a partially aspheric surface shape. According to an aspect, the optical system includes a collimating optical component disposed adjacent the proximal surface of the lens component. In an aspect, an optical cover is disposed at least over the cavity in the distal surface of the lens component. An index-matching medium may be disposed immediately adjacent at least a portion of the distal surface of the lens component. The optical system may be a target illumination and non-imaging target emission-collection system for quantifying fluorescence emission. The optical system may further include, by reference, other attributes referred to in other embodiments of the invention that are not expressly recited in conjunction with the instant embodiment.

Another embodiment of the invention is directed to an optical system disposed in, or at, a distal end of a fluorescence emission endoscope apparatus, that includes an objective lens component having a clear central aperture, disposed adjacent a distal end of the endoscope, wherein the objective lens component transmits at least a visible light spectrum or a fluorescence emission from a target. According to an aspect, at least a portion of at least a proximal surface or a distal surface of the lens component has a coating to achieve a desired optical effect. According to an aspect, a distal lens is fixedly disposed in the clear aperture of the lens component. According to various aspects, the proximal surface of the lens component has a spherical shape or an aspheric shape, and the distal surface of the lens component has a flat surface, at least a partially spherical surface shape, or at least a partially aspheric shape. According to an aspect, the optical system includes a collimating optical component disposed adjacent a proximal side of the lens component and aligned along an optical axis passing through the clear aperture of the lens component. In an aspect, an optical cover is disposed over at least the clear aperture on the distal surface of the lens component. According to an aspect, the optical system is a target illumination and non-imaging, target emission-collection system. The optical system may further include, by reference, other attributes referred to in other embodiments of the invention that are not expressly recited in conjunction with the instant embodiment.

Another embodiment of the invention is directed to a dual magnification optical system disposed in, or at, a distal end of a fluorescence emission endoscope apparatus. The optical system includes a high-magnification target illumination path that transmits light in a near infra-red (IR) spectral region from a fluorescence emission-exciting target illumination source to a target; a dual, integrated low-magnification target illumination path and fluorescence emission path that transmits light in a visible spectral region from a visible light illumination source to the target and, which, transmits fluorescence emission from the target towards a proximal region of the endoscope, respectively. According to an aspect, the dual, integrated low-magnification target illumination path and fluorescence emission path further comprises an integrated, low-magnification visible target emission path that transmits visible emission from the target towards the proximal region of the endoscope. According to an aspect, the optical system further comprises an objective lens component fixedly disposed adjacent a distal end of the endoscope, wherein only a portion of the lens component transmits the high-magnification target illumination and only a different portion of which reflects the high-magnification target illumination; further wherein at least a portion of the lens component forms at least a part of the dual, integrated low-magnification target illumination path and the fluorescence emission path. In a related aspect, the portion of the lens component that transmits the fluorescence emission-exciting target illumination consists of an uncoated region of a proximal surface of the lens component and an uncoated region of a distal surface of the lens component, further wherein the different portion that reflects the high-magnification target illumination consists of a coated region of the proximal surface of the lens component and a coated region of the distal surface of the lens component. According to an aspect, the portion of the lens component that forms at least a part of the dual, integrated low-magnification target illumination path and fluorescence emission path comprises at least a portion of the uncoated region of the distal surface of the lens component and at least a portion of the coated region of the proximal surface of the lens component. In an aspect, the system further comprises a collimating lens disposed in the fluorescence emission-exciting target illumination path adjacent the lens component. According to an aspect, a distal lens is disposed immediately adjacent at least a portion of the distal surface of the lens component. In a related aspect, the distal lens is disposed immediately adjacent the coated region of the distal surface of the lens component. According to an aspect, the optical system is a target illumination and non-imaging, target emission-collection system. The optical system may further include, by reference, other attributes referred to in other embodiments of the invention that are not expressly recited in conjunction with the instant embodiment.

An embodiment of the invention is directed to an optical system module for use in, or with, a fluorescence emission endoscope apparatus. The optical system module includes a housing assembly having a proximal end adapted to be connected to a distal end of the fluorescence emission endoscope; an objective lens component disposed adjacent a distal end of the housing, wherein the objective lens component has a proximal surface that is only partially coated with a patterned coating that at least one of selectively reflects and transmits a target illumination and selectively transmits and reflects a target emission, and a distal surface that is only partially coated with the coating. According to an aspect, the housing incorporates a light pipe that transmits the target illumination and the target emission. In a related aspect, the housing comprises a transparent seal disposed in the proximal end of the housing. According to an aspect, the housing encloses a gaseous environment. According to an aspect, the optical system module further comprises a scanner disposed adjacent the proximal end of the housing, wherein the scanner has a target illumination input adapted to receive target illumination light from a target illumination source and a target illumination output. In a related aspect, the target illumination output comprises an optical waveguide having a distal output end. The lens component forms a conjugate image of the distal end of the waveguide at the target. According to an aspect, the optical system module further comprises a collimating lens disposed intermediate the distal end of the waveguide and the proximal surface of the lens component. The optical system module may further include, by reference, other attributes referred to in other embodiments of the invention that are not expressly recited in conjunction with the instant embodiment.

Another embodiment of the invention is directed to an optical system module for use in, or with, a fluorescence emission endoscope apparatus, that includes a removably connectable housing assembly having a proximal end adapted to be connected to a distal end of the fluorescence emission endoscope apparatus, and an objective lens component having a clear central aperture, disposed adjacent a distal end of the housing, wherein the objective lens component transmits at least a visible light spectrum or a fluorescence emission from a target. According to an aspect, at least a portion of at least a proximal surface or a distal surface of the lens component has a coating to achieve a desired optical effect. According to an aspect, the optical system module further includes a distal lens fixedly disposed in the clear aperture of the lens component. In various related aspects, the proximal surface of the lens component has a spherical or an aspheric shape, and the distal surface of the lens component has a flat surface, an at least partially spherical surface shape, and an at least partially aspheric surface shape. According to an aspect, an optical cover is disposed over at least the clear aperture on the distal surface of the lens component. In a related aspect, the housing comprises a transparent seal disposed in the proximal end of the housing. The housing may enclose a gaseous environment. According to an aspect, the optical system module further includes a scanner disposed adjacent the proximal end of the housing, wherein the scanner has a target illumination input adapted to receive target illumination light from a target illumination source and a target illumination output. In an aspect, the target illumination output comprises an optical waveguide having a distal output end. The lens component forms a conjugate image of the distal end of the waveguide at the target. According to an aspect, the optical system module further comprises a collimating lens disposed intermediate the distal end of the waveguide and the proximal surface of the lens component. The optical system module may further include, by reference, other attributes referred to in other embodiments of the invention that are not expressly recited in conjunction with the instant embodiment.

An embodiment of the invention is directed to an optical waveguide-based, fluorescence emission endoscopy system that includes one or more optical waveguides having a distal end; and an optical system disposed in, at, or adjacent the distal end of at least one of the one or more optical waveguides, wherein the optical system includes an objective lens component having a proximal surface that is only partially coated with a patterned coating that at least selectively reflects or transmits a target illumination or selectively transmits or reflects a target emission, and a distal surface that is only partially coated with the coating. The endoscopy system may further include, by reference, other attributes referred to in other embodiments of the invention that are not expressly recited in conjunction with the instant embodiment.

An embodiment of the invention is directed to a method for remotely-controlled, multi-magnification imaging of a target with an endoscope assembly. The method involves the steps of providing an optical system disposed in a distal end of the endoscope assembly; providing a high-magnification target illumination path that transmits pulsed light in a near infrared (IR) spectral region from a high-magnification target illumination source through only a designated portion of the optical system and out of the distal end of the endoscope assembly; and, providing a dual, integrated low-magnification target illumination path and fluorescence emission path as well as a visible back-scattered light path that transmits light in a visible spectral region from a visible light illumination source through a different designated portion of the optical system and out of the distal end of the endoscope assembly to the target and, which, transmits fluorescence emission from the target through the different designated portion of the optical system towards a proximal region of the endoscope assembly, respectively. The method may further include, by reference, other attributes referred to in other embodiments of the invention that are not expressly recited in conjunction with the instant embodiment.

The embodiments described herein take advantage of the fact that the fluorescence emission excitation field is typically in the near IR (~700 nm<$\lambda$≤1.3µ) spectrum; thus the excitation wavelength can be easily separated from the substantially shorter fluorescence emission wavelengths and the visible light (~400 nm≤$\lambda$≤700 nm) for viewing at low magnification. Furthermore, since the 3D resolution of multiphoton imaging results entirely from the scanned laser excitation, the fluorescence emission collection optical system requires only the capability to provide efficient emitted signal collection, facilitating the use of a simple, large aperture lens rather than a highly corrected objective lens. The non-confocal design of the high-magnification optical system provides added advantage for imaging deep in tissue because the problem of image obstruction from a concentric fiber scanner is reduced, as is the concern that the excitation fiber will not provide sufficiently efficient signal collection and/or transmission.

The various apparatus and method embodiments will be applicable to both flexible and rigid endoscopes, as well as to general multiphoton and optical harmonic generation fluorescence emission processes.

In various exemplary applications, the apparatus and method embodiments described herein can be used to provide in vivo, in situ microscopic imaging of the infrastructure and bio-chemistry of tissue as a shortcut to diagnostic information that ordinarily would be later acquired by a pathologist's hematoxylin and eosin (H&E) stained absorption microscopy of fixed thin slices of tissue obtained by biopsy. The embodied apparatus and methods of the present invention may be utilized during surgery or during precursor diagnostics to delineate boundaries of malignant tumors or to recognize particular disease or damaged states, which will inform their prompt treatment, and for monitoring past treatment results. The embodied apparatus and methods may be used to identify and recognize organs and anatomical structures to be protected from injury during surgery, such as nerve bundles, microtubule bundles, and other structures. The embodied apparatus and methods will allow accurate spatial target discrimination, and permit non-imaging quantification of fluorescence emission from target volumes.

It will be appreciated by those skilled in the art that quantitative fluorescence emission collection as well as fluorescence emission images may be collected at various angular and rotational orientations of the optical systems according to various embodiments, as known in the art for conventional endoscopic imaging.

BRIEF DESCRIPTION OF THE DRAWINGS

The accompanying drawings illustrate various exemplary and illustrative embodiments and aspects of the invention. In the drawings.

DETAILED DISCUSSION OF CERTAIN DESCRIPTIVE, ILLUSTRATIVE, AND EXEMPLARY EMBODIMENTS OF THE INVENTION

Embodiments of the invention pertain generally to fluorescence emission endoscopy systems and methods.

Figure 1:
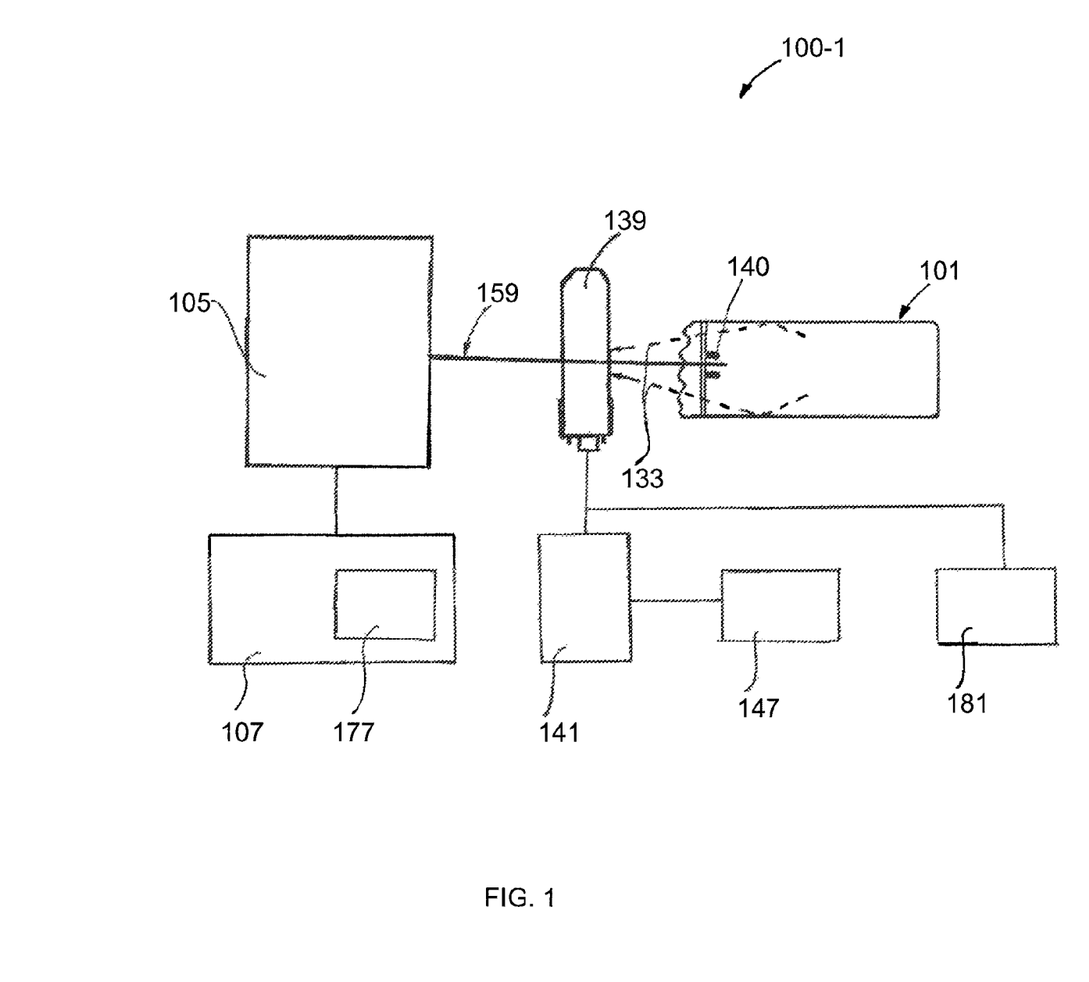
FIG. 1 is a schematic drawing of an endoscopy system, showing various illumination, control, detection, and analysis components including the distal end of a coaxial endoscope incorporating an optical system according to an illustrative embodiment of the invention.

FIG. 1 shows a schematic diagram of a coaxial endoscope system 100-1 that is shown with a distal segment 101 that incorporates an optical system embodied by the invention. As described herein, the distal segment can be that of an endoscope or alternatively, may be a biopsy needle. The system is coaxial because, as shown, an optical fiber 159 that provides near IR target excitation light is coaxially surrounded, in part, by a light transmitting interior of the distal segment 101. The fluorescence emission endoscopy system 100-1 includes an illumination platform 105 that includes a suitable fluorescence emission excitation source such as a femtosecond, pulsed laser and a source of visible target illumination. An illumination platform control module 107 provides, for example, pulse shape control, beam expansion, spatial filtration, spectral phase control, modulation, and other control functions for the target illumination sources. Light source control module 107 may also include wavelength source control module 177 to adjust and switch wavelengths generated by the IR source. The system thus has at least a dual wavelength band target illumination capability that in conjunction with the optical system described herein, can provide remotely-controlled, multi-magnification fluorescence emission imaging and signal detection. As further shown in FIG. 1, a detector component 139 is provided for collecting fluorescence emission and other signal light (collectively, 133) from the target (not shown). The detector component 139 may be a photomultiplier tube (PMT) or other appropriate detector mechanism or imager that recovers visible signal light as well as fluorescence emission for non-imaging or imaging applications. A scanner 140 is shown disposed in the distal segment 101 according to an exemplary embodiment described in further detail below. The system also includes a detection control module 181 to control detection and collection of signal light from distal segment 101, a target analysis module 147, and a computer-controlled display device 141.

Figure 2:
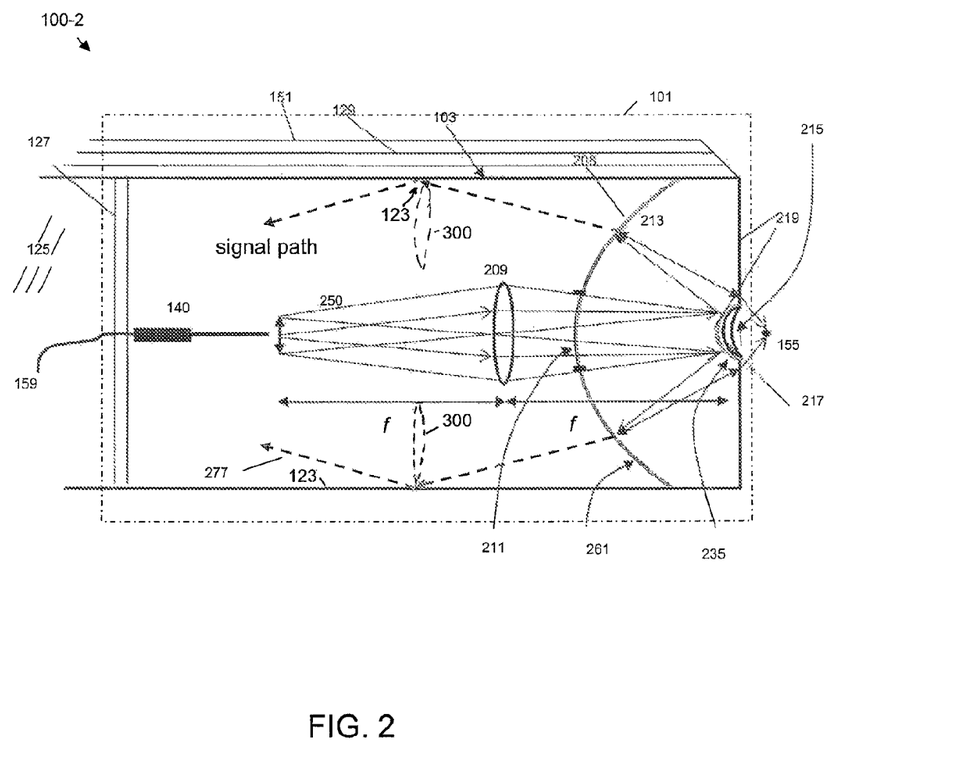
FIG. 2 is a side, cross sectional, schematic view of the distal segment of an endoscope incorporating an optical system in accordance with an illustrative embodiment of the invention.

FIG. 2 provides an illustration 100-2 of the distal segment 101 according to an exemplary embodiment of the invention. In the aspect shown, distal segment 101 represents the terminal, distal end of a micro-endoscope for imaging a target 155.

As shown, an objective lens component 213 is fixedly disposed in a terminal, distal endoscope segment 101. The objective lens component has a proximal surface 208 having a circumferentially-patterned dichroic coating as shown by the bolded line 261. A central region 211 of the proximal surface 208 is uncoated or may be anti-reflection coated. The lens component 213 has a distal surface 219 that is concave in a central region and otherwise having a different curvature (including flat) out to the periphery of the lens. The concave central region thus forms a finite cavity 217 in the central region of the distal surface. The concave region of the distal surface also has the dichroic coating as shown by the bolded line 235. A fiber 159 delivers short, high-repetition pulses of 780 nm target illumination 250 to scanner 140. A collimating lens 209 is disposed along the central longitudinal axis of the distal segment 101 and directs the scanned illumination 250 to the uncoated or anti-reflection coated central region 211 of the lens component. The light is reflected from the dichroic-coated central region 235 of the distal surface of the lens back towards the circumferentially-coated region 261 of the proximal surface. The light is then refracted out through the uncoated region of the distal surface of the lens to illuminate the target 155. The dichroic coating, on the lens component is designed to also transmit visible light that is used to illuminate the target and which is reflected/scattered from the target as visible signal light.

In the illustrative embodiment of FIG. 2, the optical system optionally includes a distal lens 215 that is disposed in the cavity 217 in the distal surface 219. The distal lens is uncoated and aids in the low magnification, large field of view, visible imaging of the target described further below. It will be appreciated, however, that the distal surface of the objective lens component 213 will provide a simple, large aperture for efficient signal collection, since the 3D resolution of multiphoton imaging results entirely from the scanned laser excitation. In an alternative aspect as shown, optional lens elements 300 (shown in dotted lines) can be added to further enhance the collection efficiency for signals.

Upon suitable excitation, the target emits multiphoton fluorescence or second harmonic generation. This fluorescence emission 277 is collected by the lens component 213 and propagates along a fluorescence emission light path within the distal segment 101 towards a detector (not shown) to provide a high-magnification, high-resolution fluorescence emission image of the target.

The illumination may be remotely controlled to provide visible target illumination. The visible illumination will pass through 209, 211, 235 and optionally 217, forming a low magnification widefield view of the target. The visible light reflected from the target is collected by the distal lens 215 and the lens component 213 and propagates along a visible emission light path within the distal segment 101 towards a detector (not shown) to provide low-magnification, wide field of view image of the target.

Figure 4A:
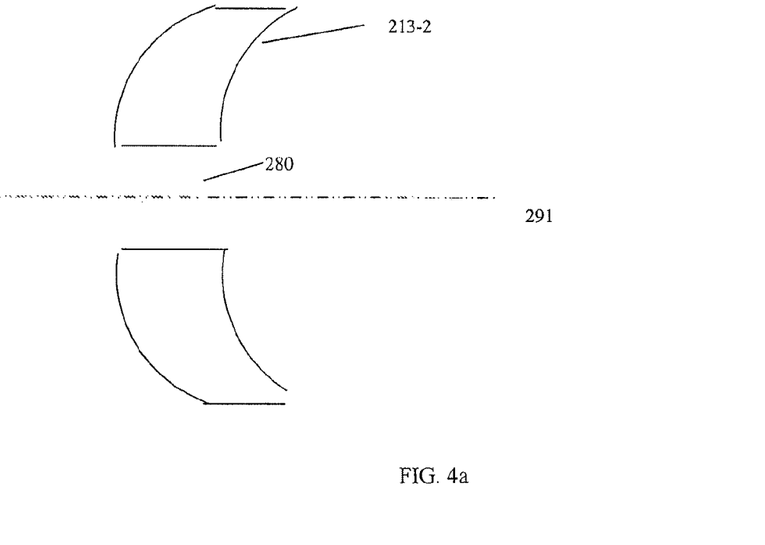
FIGS. 4a and 4b are schematic drawings of alternative aspects of an objective lens component according to illustrative aspects of the invention.
Figure 4B:
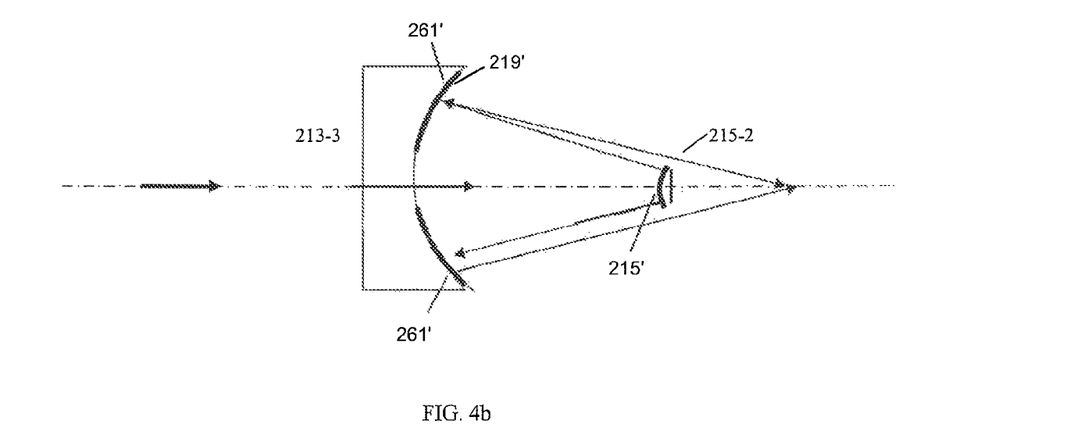

It will be appreciated that the pattern arrangement of lens surface coatings, the optical characteristics of the lens/lenses, the optical system layout, and other attributes of the embodiments can be varied without departing from the scope of the invention. The embodiment provides a multi-magnification, multi-integrated-optical path, and integrated dual-imaging optical component, optical system for fluorescence emission/visible imaging. FIGS. 4a and 4b show illustrative alternative aspects of the optical system involving an objective lens component and a distal lens. For example, FIG. 4a shows a side cross sectional profile of an annular lens component 213-2. A clear central aperture 280 surrounds the optical axis 291 of the lens. A dichroic coating can be patterned on various regions of the lens to accomplish the desired dual imaging function of the lens. In FIG. 4b, distal lens 215-2 is disposed along the optical axis adjacent the distal surface 219' of the lens component 213-3. As shown, the proximal surface 215' of distal lens 215-2 and a peripheral region 261' of distal surface 219' of lens component 213-3 are coated to reflect incident IR target excitation light after it passes through the uncoated central region of lens 213-3. The lens system will provide integrated multi-path, multi-magnification fluorescence/visible imaging as described herein above.

As further shown in FIG. 2, one embodiment of the distal segment 101 may incorporate a light pipe 103 having a reflecting inner wall 123 that seals an air core of the distal segment. In the aspect shown, an outer cladding layer 151 surrounds the light pipe. A transmissive cover 127 is disposed in a proximal end of the distal segment 101. The cover 127 separates the low index air core of the distal segment 101 from a higher-index medium 125 of the endoscope body and provides support for the scanner 140. The cover may be coated to better transmit the fluorescence emission 277. The higher index medium 125 of the endoscope body is surrounded by a lower index outer cladding to form a light guiding pipe for the signal fluorescence. Suitable light pipe designs are well known to people skilled in the art. The endoscope body may be flexible or rigid.

In another embodiment, the distal segment 101 may incorporate additional lenses 300 positioned in-between the cover 127 and the objective lens 213. In the exemplary embodiment shown in FIG. 2, lenses 300 may be constructed in an annular form with a central region designed for the passage of the excitation light and an outer region for the collection of the fluorescence. Lenses 300 may increase the fluorescence collection efficiency of the endoscope system.

The air core 121 of segment 101 may accommodate other simple fiber scanners. Suitable fibers include, but not limited to, air core photonic bandgap fibers, higher order mode fibers, microstructure fibers and large core broadband fibers. Other probes may be used depending upon the type of scanner and cladding layer 151 employed. Additionally, the laser beam transmitted via optical fiber 159 may also be scanned with oscillating mirrors or micro-electromechanical systems (MEMS) and the like.

Figure 3:
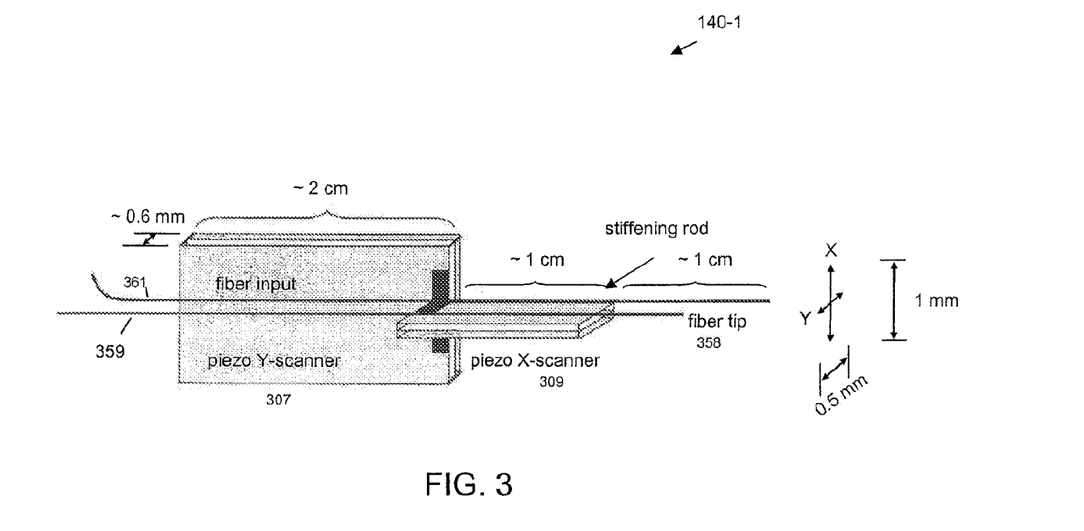
FIG. 3 is a schematic illustration of a fiber X-Y scanner that could be used in an exemplary embodiment of the invention.

FIG. 3 illustrates an exemplary fiber X-Y scanner 140-1. The scanner comprises two piezo bending elements, a piezo X-axis scanner 309 and a piezo Y-axis scanner 307, to drive the IR raster scan of the fiber tip 358. The scanner 140-1 includes a first fiber 359 for transmitting the near IR excitation light and high-magnification signal light, and a second fiber 361 for transmitting the visible target illumination, locating the excitation light focus, and low-magnification viewing. Both fibers are disposed on the same (X) scanner and each has a different overhang length as shown. The fiber tip 358 will typically be conjugately imaged onto the target by the optical system. The fast (X) axis scanner 309 will be driven resonantly, while the slow (Y) axis scanner 307 will be driven non-resonantly. Exemplary physical dimensions of the scanner and the scan ranges are indicated in the figure.

Fluorescence imaging deep in tissue may be performed using a gradient refractive index (GRIN) lens as reported in the art. An optional GRIN lens may be incorporated in the coaxial optical system 100-1 as a distal attachment near distal lens 215 using additional optical geometries.

As mentioned above, a high refractive index medium 125 helps to provide low loss propagation of the fluorescence emission 277 to a detection platform 139 at the proximal end of the endoscope or other diagnostic device. Typical refractive index values can range from approximately 1.58 to 1.73. Additionally, a flexible, low refractive index tube 129 can be concentrically disposed around the light pipe 103 to assist in positioning the distal endoscope end.

In an exemplary aspect, the light pipe 103 is approximately 5 mm in diameter, but other diameters may be practical. For example, 8 mm diameter systems may be used in diagnosing and monitoring treatment of bladder cancer by endoscope entry thorough the ureter. In addition to urological applications, laparoscopic tools for prostate examination and cancer and other surgeries may also utilize the system and method of the present invention. Further, in colonoscopy procedures, large diameter flexible endoscopes may provide color sensitive low magnification video imaging of the tissue to guide the fluorescence emission imaging. Similarly, small diameter systems may be used in optical biopsy environments.

It will be further appreciated that various protective external shells that accommodate both rigid and flexible endoscopes can be incorporated with the disclosed embodiments of the invention.

Figure 5:
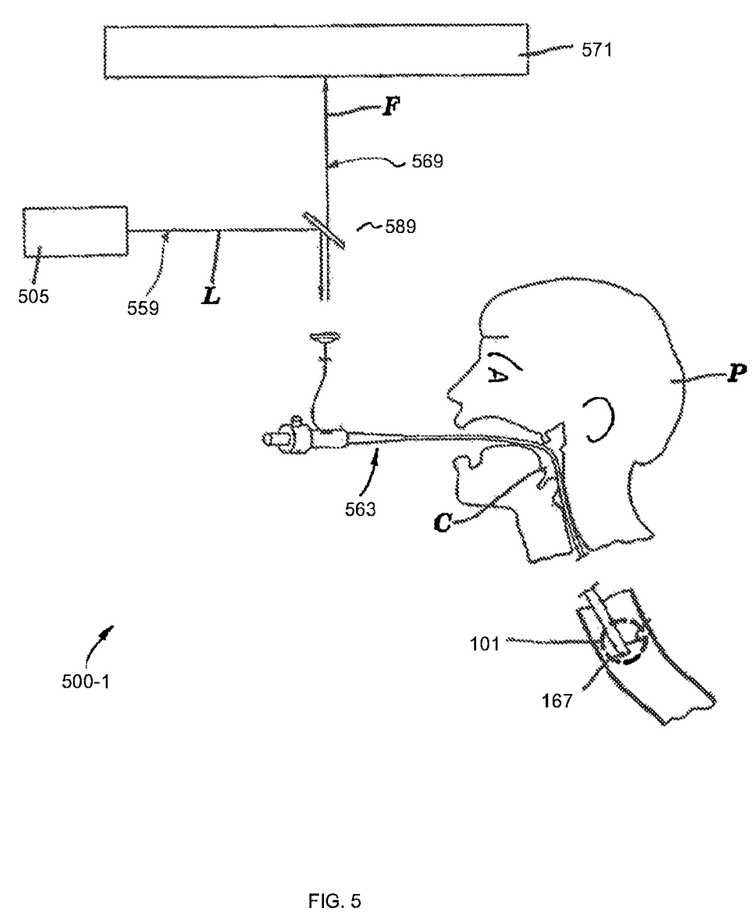
FIG. 5 is a schematic drawing of an endoscopy application according to an illustrative embodiment of the invention.
Figure 6:
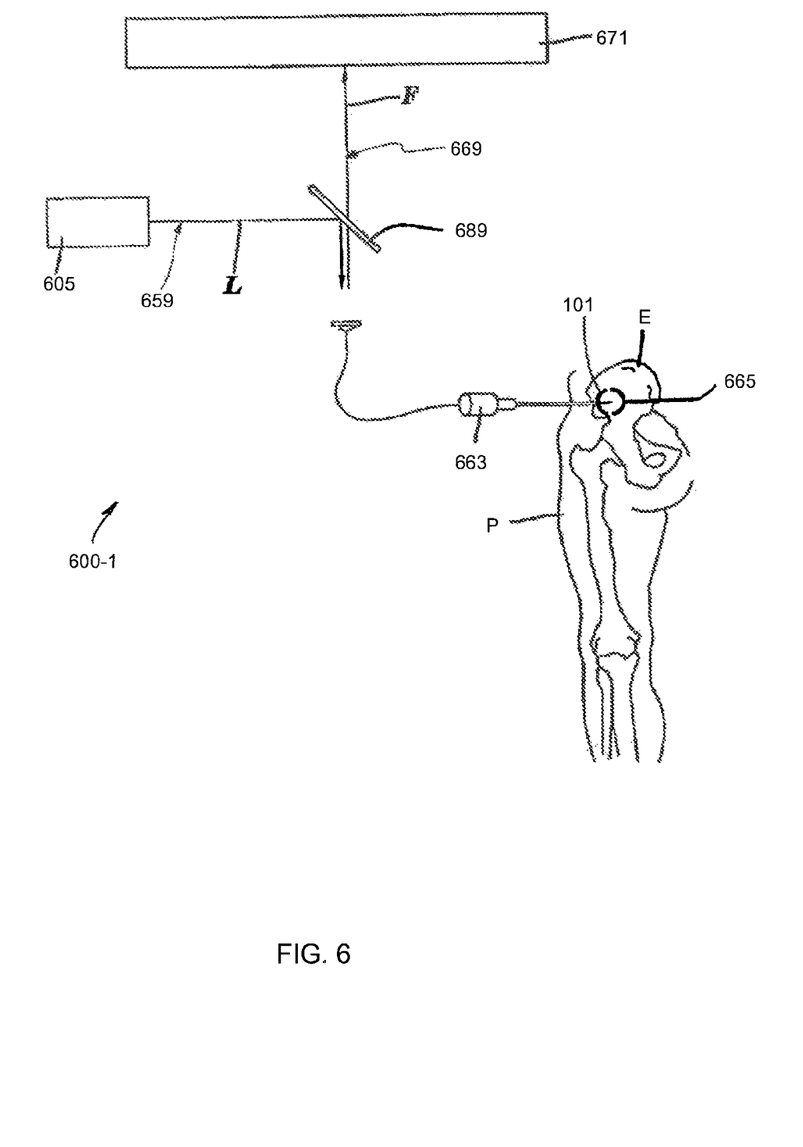
FIG. 6 is a schematic drawing of an endoscopy/needle biopsy application according to an illustrative embodiment of the invention.

FIGS. 5 and 6 show schematic views of two application environments in which the apparatus and method embodiments of the present invention may be used. The coaxial endoscopy system of the present invention performs fluorescence imaging, processing, and measurements of intrinsic fluorescence of a target as embodied in various medical endoscope and optical biopsy needle architectures.

FIG. 5 shows an endoscope arrangement 500-1 in accordance with the present invention, while FIG. 6 shows an optical biopsy needle arrangement 600-1 in accordance with the present invention. FIGS. 5 and 6 are presented to illustrate how the distal optics assembly of the present invention may be used in a number of clinical settings.

Referring to FIG. 5 (with reference to FIG. 1 as described above), an endoscope arrangement 500-1 includes a laser light source 505 that produces laser illumination L, which is transmitted to distal segment 101 through optical fiber 559. The distal segment 101 is housed in endoscope 563. The distal end of endoscope 563 is passed, for example, into the mouth of patient P through cavity C which, in this case, is the esophagus. Fluorescence emission F and scattered visible light are detected and transmitted by the segment 101 as described herein above and are passed through dichroic mirror 589 and through detection path 569 into spectroscopic and/or imaging detection equipment 571 to provide a high magnification, high spatial resolution image using the fluorescence emission and a low magnification, low spatial resolution image using the scattered visible light.

Spectroscopic and/or imaging detection equipment 571 may include the detection platform 139 (shown in FIG. 1), including a PMT or other detection device, and a computer based video display 141 for detection and digital transmission to a computer for image formation and display.

Another embodiment of the present invention is based on penetration of tissue itself with either at least one conventional optical fiber or with an optical biopsy needle. Optical needle biopsy uses sub-mm diameter needles for light pathways. Surgical needle biopsy may be used as a diagnostic procedure, for example, in lung cancer and breast cancer diagnoses. The needle may be guided by CT scanning to direct the needle to the desired locations. Biopsy tissue is removed and is subjected to H&E staining for absorption microscopy. A sub-mm diameter biopsy needle may be too small to permit optical imaging but may facilitate femtosecond laser transmission through the needle bore and collection of the fluorescence emission back through the needle, allowing quantitative measurement of emission spectra, which may be used as a diagnostic tool to identify structures (e.g., collagen) by SHG and metabolic states by intensity of nicotinamide adenine dinucleotide (NADH). Quantitative correlation of the intrinsic fluorescence spectra of tissue generated in MPM may be compared to biopsy specimens as when using the system and method of the present invention in an endoscopic environment.

In the optical biopsy needle application illustrated in FIG. 6, the needle incorporating an optical system in its distal end as disclosed herein is inserted into the tissue to sample the autofluorescence of the tissue at the end of the needle. The distal segment of the needle can function as a hypodermic syringe that may be inserted into the tissue as needed. Alternatively, the distal segment can be configured to abut the surface of the tissue being imaged. With multiphoton excitation, the focal volume at the end of the needle where fluorescence is excited is well defined. Alternatively, a bundle-type needle could be used to illuminate a larger tissue volume. In performing biopsies of dense tissue cancers, such as breast or liver cancer, the needle endoscope can be used to examine fluorescence along insertion pathways. In contrast to conventional biopsies, which generally require time-consuming tissue fixing and staining procedures, the optical biopsy with multiphoton excited fluorescence spectroscopy provides immediate diagnostic spectral data as the needle is inserted and moved within the patient.

As further shown in FIG. 6, (with reference to FIG. 1), an optical biopsy needle arrangement 600-1 includes laser light source 605 that produces laser illumination L, which is transmitted to distal segment 101 through optical fiber 659. In the biopsy needle arrangement, distal segment 101 is housed in the bore of optical biopsy needle 663. The distal end of optical biopsy needle 663 is passed, in this example, through the skin of patient P and into pelvis E. Multiphoton fluorescence F and scattered visible light are detected and transmitted by the optical system as described above and are passed through dichroic mirror 689 and through detection path 669 into spectroscopic and/or imaging detection equipment 671 to provide a high magnification, high spatial resolution image using the multiphoton fluorescence and a low magnification, low spatial resolution image using the scattered visible light.

Spectroscopic and/or imaging detection equipment 571 may include detection platform 139 (shown in FIG. 1), including a PMT or other detection device, and a computer based video display 141 for detection and digital transmission to a computer for image formation and display.

These form aspects of the coaxial endoscopy system of the present invention can also be carried out in combination where an endoscope is inserted into a body cavity of a patient to provide a route for fibers to reach an internal surface of a body cavity from which the fibers can be inserted into a tissue material to sample its successive layers. For example, in the search for the onset of cancer in the wall of the colon, the tissue has about 5 layers, each with its own characteristic optical properties and autofluorescence. Successive optical probing of each layer can distinguish the different layers and recognize their changes by disease. These forms of multiphoton medical imaging may be used to replace traditional biopsy assays by imaging inside a body cavity or solid tissue to provide immediate evaluation and treatment adjustment with local anesthesia on an outpatient basis. The apparatus and methods of the present invention activate a tissue material by applying radiation to promote a simultaneous multiphoton excitation of the tissue to emit an intrinsic fluorescence characteristic. The intrinsic fluorescence is compared to fluorescence emitted by exciting healthy tissue under the same conditions, and the results are compared to determine if the examined tissue is potentially diseased.

Detection of the multiphoton excited fluorescence and the second and third harmonic of the laser excitation generated in the tissue can be accomplished by endoscopy and optical biopsy through the segment that provides the excitation and signal path and through additional surrounding fibers in a bundle or through thicker optical tubes for efficient collection of light that is excited near the tip of a single mode excitation fiber or fibers. There is a significant advantage in fluorescence collection efficiency for multiphoton endoscopic tissue fluorescence over single photon excitation, because the emission is localized near the tip of the optical fiber where it is most accessible to the coaxial optical instrumentation. The same advantage applies in optical biopsy needle environments.

Effective multiphoton molecular excitation is made possible by the combination of both the very high, local, instantaneous intensity and the temporal concentration of a pulsed laser light source. For example, a high intensity IR source such as a titanium sapphire mode locked solid state laser, with pulse duration of about 100 femtoseconds ($100 \times 10^{-15}$ seconds) and a pulse repetition rate of 80 MHz may advantageously be used. Pulses of light having a wavelength between about 700-1000 nm, or with the pulses having a width of $10^{-9}$ seconds to $10^{-15}$ seconds are advantageously suitable. Other lasers that are also effective for multiphoton excitation and harmonic generation can also be used. These lasers may be used to produce light at different relatively long wavelengths in the infrared or visible red region of the spectrum, for example, to generate the necessary excitation photon energies that will add up to the appropriate absorption energy band required by the fluorophores in the spectrum that normally would be excited by absorption of a single photon in the spectral region having wavelengths about one-half the wavelength of the incident light. If shorter excitation wavelengths are needed, the laser wavelengths can be divided by 2, 3, or 4 by external harmonic generation. Thus, for example, two photons in the visible red region at 750 nm would combine to excite a fluorophore that normally absorbs light in the ultraviolet region at or above 375 nm, while two photons in the infrared region of, for example, 1070 nm, would excite a fluorophore which absorbs at or above 535 nm in the visible light region. These fast pulses are directed through the endoscope or optical biopsy needle to target tissue material or to a tissue specimen. Because of the high instantaneous power provided by the very short duration focused pulses, there is an appreciable probability that a fluorophore (a fluorescent dye), contained in the target tissue material, and normally excitable by a single high energy photon having a short wavelength, typically ultraviolet, will absorb two long wavelength photons from the laser source simultaneously. This absorption combines the energy of the two photons in the fluorophore molecule, thereby raising the fluorophore to its excited state. When the fluorophore returns to its normal state, it emits light, and this light then passes back through the endoscope or optical biopsy needle to a suitable detector.

In addition to measurement of intrinsic tissue fluorescence with multiphoton excitation, it is possible to utilize the fluorescence of drugs to detect their location in tissue. Often, such drugs segregate to particular tissue structures or disease products, such as tumors. Multiphoton excitation can be used to identify them. Many important drugs absorb ultraviolet light to become fluorescent and are, therefore, effectively excited by multiphoton excitation. As a result, all of the advantages of multiphoton excitation of intrinsic tissue fluorescence together with the labeling features provided by the selective segregation or binding of fluorescence drugs are achieved. For example, the principal drug used to treat colitis, 5-amino salicylic acid, can be imaged in all of the layers of living colon tissue explants as the drug is metabolized. It can be located relative to complex tissue structure by imaging tissue autofluorescence due to collagen, nicotinamide adenine dinucleotide (NADH), and other structures. Multiphoton excitation of such drugs can be observed in vivo within tissues by multiphoton endoscopy and/or multiphoton optical biopsy.

Photoactive agents including fluorescent dyes are commonly used in multiphoton microscopy to image properties of cells and tissues. Suitable photoactive agents include dyes which are excited by multiphoton excitation such as, organic molecules whose fluorescence changes when they bind metal ions such as $Ca^{2+}$, $Mg^{2+}$, $Na^+$, $K^+$, or $H^+$. Dyes that bind to the DNA double helix such as DAPI (4',6-diamidino-2-phenylindoledihydrochloride) are particularly useful. Many such dyes are suitable for application in vivo.

Fluorescence distribution may also be probed by multiphoton absorption endoscopic spectroscopy in living animals, including humans, to recognize inflammatory disease such as colitis and to follow the progress of its treatment. The distribution of fluorescent protoporphyrin IX, the metabolic product of amino evulinic acid, which accumulates in cancer cells, would similarly be useful in cancer detection. NADH fluorescence may be the most promising cancer signal accessible by multiphoton absorption endoscopic spectroscopy, but it must be spatially localized by multiphoton absorption to distinguish it from other sources including collagen, which can be similarly fluorescent in adjacent tissues. Certain tissues and tissue components, particularly collagen, an important structural component of tissue that appears in many forms, are very effective at generating the second harmonic of bright coherent illumination. The second harmonic of illumination has exactly half of the wavelength and thus twice the photon energy of the fundamental illumination. Similarly, the third harmonic of illumination has exactly one third of the wavelength and, therefore, three times the photon energy. Generation of second harmonic radiation has been demonstrated to be a useful phenomenon for microscopic imaging of cells. Because the illumination conditions required to excite second or third harmonic in complex tissue are nearly the same as for multiphoton fluorescence excitation, it is possible to take advantage of second or third harmonic generation, in tissues such as collagen, to complement multiphoton excitation of intrinsic tissue fluorescence. In complex tissues, the second or third harmonic radiation is frequently radiated through broad angles that make it detectable along with the multiphoton excited fluorescence.

The apparatus and method of the present invention may be used for a variety of purposes. For example, histological and clinical composition, structure, metabolic state, and vitality in the region of the subject can be determined. Alternatively, functional response to physiological and pharmacological stimuli and disease states can be detected in the region of the subject. Further, tissue or drug fluorescence excitation and emission spectra, luminosity, fluorescence lifetime, and temporal fluctuations in the region of the subject may also be determined.

The external geometries of urological endoscope configurations for imaging and biopsy in the bladder include outside diameters of approximately 4.5 mm and 8 mm. An optical tube may contain a series of rod lenses that illuminate an area on the inside of the bladder wall for low magnification surface imaging and collect backscattered and reflected light from tissue surfaces and deliver the light to an eyepiece or camera. A small tube for fluid perfusion and insertion of wire catheters and other catheters may also be included. An endoscope aspect of the present invention includes a fiber input for pulsed infrared laser light for MPM and white light for low magnification illumination, as well as a light pipe guiding both sources of the imaging light to an imaging detector, such as a PMT or the like.

The foregoing description of the aspects and embodiments of the present invention provides illustration and description, but is not intended to be exhaustive or to limit the invention to the precise form disclosed. Those of skill in the art will recognize certain modifications, permutations, additions, and combinations of those embodiments are possible in light of the above teachings or may be acquired from practice of the invention.

We claim:

1. An optical system, comprising:
a one-piece objective lens component having an external proximal surface on an image side and an external distal surface on an object side adjacent an intended object or target optical space, wherein a central region of the external distal surface of the lens component has a cavity.

2. The optical system of claim 1, wherein the cavity has a curvature that is different than a curvature of the proximal surface.

3. The optical system of claim 1, wherein the one-piece objective lens component includes a different lens fixedly disposed adjacent the cavity in the central region of the external distal surface of the objective lens component.

4. The optical system of claim 3, wherein the different lens is disposed immediately adjacent the cavity.

5. The optical system of claim 1, wherein the proximal surface is only partially coated with a patterned coating that at least one of selectively reflects or transmits a target illumination and selectively transmits or reflects a target emission, and the distal surface is only partially coated with the coating.

6. The optical system of claim 1, wherein only a portion of one of the proximal surface and the distal surface has a dichroic coating and only a different portion of one of the distal surface and the proximal surface has the dichroic coating.

7. The optical system of claim 6, wherein the lens reflects or transmits a first spectrum and transmits or reflects a second, different spectrum.

8. The optical system of claim 6, wherein the coating reflects light in an IR spectrum and transmits light in at least one of a visible spectrum and a spectrum of wavelengths shorter than the IR spectrum.

* * * * *